United States Patent [19]

Armstrong

[11] Patent Number: 4,864,042
[45] Date of Patent: Sep. 5, 1989

[54] PROCESS FOR PREPARING SILVER CATALYSTS

[75] Inventor: William D. Armstrong, Stamford, Conn.

[73] Assignee: Scientific Design Company, Inc., Little Ferry, N.J.

[21] Appl. No.: 9,323

[22] Filed: Jan. 30, 1987

Related U.S. Application Data

[60] Continuation of Ser. No. 771,733, Sep. 3, 1985, abandoned, which is a division of Ser. No. 610,229, May 14, 1984, Pat. No. 4,555,501.

[51] Int. Cl.$^4$ .................................... C07D 301/10
[52] U.S. Cl. .................................................. 549/534
[58] Field of Search ........................................ 549/534

[56] References Cited

U.S. PATENT DOCUMENTS

| | | | |
|---|---|---|---|
| 3,345,199 | 10/1967 | Fitch | 106/1.24 |
| 4,012,425 | 3/1977 | Nielsen et al. | 549/534 |
| 4,177,169 | 12/1979 | Rebsdat et al. | 549/534 |
| 4,248,741 | 2/1981 | Wernli et al. | 549/534 |
| 4,321,206 | 3/1982 | Cavitt | 549/534 |
| 4,342,667 | 8/1982 | Armstrong et al. | 252/476 |
| 4,455,392 | 6/1984 | Warner et al. | 549/534 |

FOREIGN PATENT DOCUMENTS 19906  6/1971  Japan.
1533813  11/1978  United Kingdom.

OTHER PUBLICATIONS

F. L. W. McKim and A. Cambron, *Can J. of Research*, "The Catalytic Oxidation of Ethylene to Ethylene Oxide," 27, Sec. B, (11), pp. 814–827, (1949).

*Primary Examiner*—Richard L. Raymond
*Assistant Examiner*—Mock W. Russell
*Attorney, Agent, or Firm*—Kenneth H. Johnson

[57] ABSTRACT

A supported silver catalyst for the oxidation of ethylene to ethylene oxide with molecular oxygen is made by impregnating a support with a hydrocarbon solution of a silver salt of a neo-acid having 7 or more carbon atoms, substantially free of water and said neo-acid. Preferably, the hydrocarbon solvent is toluene, xylene, ethyl benzene, cyclohexane, or cumene. The impregnated support is dried and the silver is activated under conditions chosen to provide the optimum selectivity to ethylene oxide. Thereafter, the activated silver catalyst maybe impregnated with an alkali metal solution sufficient to increase selectivity of the silver catalyst above its alkali-free state. The amount of alkali metal on the finished catalyst is the optimum for the particular support selected and preferably will be about $1-6 \times 10^{-3}$ gew/kg of catalyst. The catalyst may also include additional promoters, such as the alkaline earth metals, preferbly barium.

10 Claims, No Drawings

PROCESS FOR PREPARING SILVER CATALYSTS

PRIOR ART

This is a continuation of application Ser. No. 771,733, filed Sept. 3, 1985, now abandoned, which is a division of application Ser. No. 610,229, now U.S. Pat. No. 4,555,501 filed May 14, 1984.

The invention relates generally to the vaporphase oxidation of ethylene with molecular oxygen to form ethylene oxide, a reaction of importance in the chemical industry. The reaction is usually carried out over a supported silver catalyst. The invention relates in particular to an improved method of preparing such catalysts.

Many methods of catalyst preparation have been disclosed. In their 1949 article in the Canadian Journal of Research, Vol. 27, Sec. B, No. 11, p. 815-6, McKim and Cambron list seven methods already available in the art. Many others have been disclosed since that time.

Silver should be dissolved in order for a uniform distribution of fine particles to be formed as the silver compound is decomposed during subsequent activation. This may be accomplished by using silver nitrate as was the case in early preparations of silver catalysts, since silver nitrate is highly soluble in water. Later, silver salts of relatively low molecular weight carboxylic acids were used. Generally, they are only moderately soluble in water and use of solubilizing-complexing agents such as ammonia and amines have been proposed, for example in Japanese Published Application No. 46-19606, U.S. Pat. No. 3,702,259, and G.B. No. 1,533,813. A silver salt often mentioned is silver lactate, which contains a hydroxyl group, accounting for its relatively high solubility in water, compared to other silver salts of carboxylic acids. Since it is important to prepare a very concentrated silver solution for impregnating a catalyst support, it will be apparent that silver salts of higher molecular weight carboxylic acids would not suggest themselves to one skilled in the art unless provision is made to solubilize the silver salts in aqueous solutions. The salts of higher molecular weight fatty acids such as silver stearate have been used as thickeners in preparing hydrocarbon greases, as shown in U.S. Pat. No. 2,391,842. Such silver salts have only very limited solubility in water. Despite this fact, silver salts of higher molecular weight carboxylic acids have been suggested as potential sources of silver for ethylene oxide catalysts.

Silver salts of fatty acids have been employed as antimicrobial agents. In U.S. Pat. No. 3,255,222 silver salts of various fatty acids, including capric (decanoic) acid are formed and then placed in solution by using amines and oxygen-containing organic solvents, such as alcohols. The concentration of such salts are very low and therefore would not be useful for preparing silver catalysts, which may contain up to 15% silver or more. Aqueous ammonia solutions have also been prepared (see U.S. Pat. No. 3,255,223).

Such compounds are related to the metal soaps used as driers and the like and, as shown in U.S. Pat. No. 2,807,553 they are generally water-insoluble solids, so that for many uses organic solvents are employed. Paint driers were prepared from the cobalt, manganese, and lead salts of $C_8$ to $C_{20}$ synthetic acids having tri-alkyl acetic acid configurations, as described in U.S. Pat. No. 2,955,949.

Silver neodecanoate was preferred as an ingredient in a palladium-silver mixture used to decorate ceramics in U.S. Pat. No. 4,262,040. Preparation of the silver compound was not described.

Despite the frequent reference to the use of carboxylic acid silver salts for preparing silver catalysts, use of the higher molecular weight salts is not believed to be widely practiced. More recent patent disclosures suggest that lower molecular weight salts which can be dissolved in water, such as lactic acid, or solubilized by amines such as silver nitrate or oxalate, appear to be the norm. However, it has now been found that the silver salts of higher molecular weight carboxylic acids, which are quite insoluble in water, can be employed to form active and selective catalysts by the method of preparation to be disclosed below.

SUMMARY OF THE INVENTION

A supported silver catalyst for the oxidation of ethylene to ethylene oxide is made by impregnating a support comprising alumina, silica, silica-alumina, or combinations thereof and having a surface area of about 0.2–1.5 m²gm with a hydrocarbon solution of a silver salt of a neo-acid (as hereinafter defined), the solution being substantially free of water and the corresponding neo-acid. The impregnated support then is dried and activated by heating to temperatures of about 200 to 600° C., preferably 250–500° C., for a sufficient time to produce an active fresh catalyst having an average silver particle size of about 0.1–2 microns.

A neo-acid is defined as one in which the carboxylic acid moiety is attached to a carbon atom which is directly attached to three other carbon atoms, or to other carbon atoms which are so attached. The preferred neo-acid is neodecanoic acid, but neo-acids having seven or more carbon atoms are useable.

Preferably, at least one alkali metal selected from the group consisting of Cs, K, and Rb is added to give the catalyst improved selectivity to ethylene oxide. The catalyst may also contain other promoters, such as the alkaline earth metals, preferably barium. These promoters also may be salts of neo-acids.

The silver salts of neo-acids may be prepared by various methods and in particular by reacting a silver compound with a neo-acid in the presence of a solubilizing agent, such as ethanol. The silver salt may be precipitated from solution, washed free of residual neo-acid and dissolved in a hydrocarbon solvent, preferably toluene, xylene, ethyl benzene, cyclohexane, or cumene.

The finished catalyst may contain up to about 15 wt % silver and about $8 \times 10^{-3}$ gew/kg (gew = gram equivalent weight) of the alkali metal(s), preferably 5–13 wt % silver and up to about $7 \times 10^{-3}$ gew/kg alkali metal(s), most preferably 8–11 wt % silver and about $1-6 \times 10^{-3}$ gew/kg alkali metal(s).

The support preferably is an alumina containing up to about 15 wt % silica and having a surface area up to about 2 m²/gm, particularly about 0.2–1.5m²/gm, and especially about 0.3–1.0m²/gm. The preferred supports will be capable of selectively adsorbing alkali metals from solution, and the preparation method of the invention is intended to take advantage of that property.

The amount of alkali metal(s) added will be selected to optimize catalyst performance and will be dependent upon the surface area of the support chosen. That is, more alkali metal will be used on supports which have larger surface area than on those having relatively small surface area.

The catalyst of the invention may be employed at oxidizing conditions typical of the art to prepare ethylene oxide by the vapor-phase oxidation of ethylene with improved results.

DESCRIPTION OF THE PREFERRED EMBODIMENTS

Catalyst Composition and Preparation

Preferred Catalysts prepared in accordance with this invention contain up to about 15% by weight of silver, expressed as metal, deposited upon the surface and throughout the pores of a porous refractory support. Silver contents higher than 20% by weight of total catalyst are effective, but result in catalysts which are unnecessarily expensive. Silver contents, expressed as metal, of about 5–13% based on weight of total catalyst are preferred, while silver contents of 8–11% are especially preferred.

Catalysts may be made with supports comprising alumina, silica, silica-alumina or combinations thereto. Preferred supports are those containing principally alpha-alumina, particularly those containing up to about 15 wt % silica. Especially preferred supports have a porosity of about 0.1–1.0 cc/gm and preferably about 0.3–0.8 cc/gm. Preferred supports also have a relatively low surface area, that is about 0.2–1.5 $m^2$/gm, especially 0.3–1.0 $m^2$/gm. Such surface areas are determined by the BET method [J. Am. Chem. Soc. 60, 309–16 (1938)]. Porosities are determined by the mercury porosimeter method; see Drake and Ritter, "Ind. Eng. Chem. Anal. Ed.," 17, 787 (1945). Pore diameters and pore diameter distributions are determined from the surface area measurements and the apparent porosity measurements.

The preferred support will be capable of selectively adsorbing alkali metals, particularly potassium, rubidium, and cesium from solutions of those metals. By this is meant the deposition of greater amounts of alkali metals than would be predicted by calculation from the amount and concentration of the solution absorbed by the support. The mechanism by which this is accomplished is not clear, but may involve ion-exchange with other metal ions found on the support. In this regard, it is of interest to note that published British patent application GB No. 2,043,481A teaches against the use of supports which contain ions exchangeable with the alkali metals (page 12, line 50). However, it has been found that the promotional effect of the alkali metals is enhanced when the support can selectively adsorb alkali metal ions. The present method of silver catalyst preparation includes steps which are intended to take advantage of this property of the preferred supports.

For use in commercial ethylene oxide production applications, the supports are desirably formed into regularly shaped pellets, spheres, rings, etc. Desirably, the support particles used have "equivalent diameters" in the range from 3–10 mm. and preferably in the range of 4–8 mm, which are usually compatible with the internal diameter of the tubes in which the catalyst is placed. "Equivalent diameter" is the diameter of a sphere having the same external surface (i.e. neglecting surface within the pores of the particle) to volume ratio as the support particles being employed.

The silver is added to the support by immersion of the support into a solution containing a silver salt of a neo-acid having seven or more carbon atoms and being substantially free of water and said neo-acid. The silver-containing liquid penetrates by absorption and/or capillary action into the pores of the support. A single immersion or a series of immersions, with or without intermediate drying, may be used, depending in part upon the concentration of the silver salt in the solution. To obtain catalysts having silver contents within the preferred range, suitable impregnating solutions will generally contain from 5–50 wt % of silver, expressed as metal, but supplied as silver salts of neo-acids. The exact concentrations employed, of course, will depend upon, among other factors, the desired silver content, upon the nature of the support, the viscosity of the liquid, and solubility of the neo-acid silver salt.

The impregnating medium, as already indicated, is characterized as a substantially water-free and neo-acid-free organic solution of a silver salt of a neo-acid having seven or more carbon atoms. As will be seen, a hydrocarbon solvent is employed, such as toluene, cyclohexane, xylene, ethyl benzene or cumene, which would ordinarily be water-free. Since water is considered detrimental to the preparation of silver catalysts when the method of the invention is used, it should be present in no more than about 0.1 vol. percent in the silver impregnating solution, preferably less than about 0.01 vol. percent.

While higher molecular weight organic acids have been mentioned in the past as usable for preparing silver catalysts, it will be clear from the examples given in the prior art that much lower molecular weight acids, such as lactic acid (hydroxy propionic acid) or oxalic acid are preferred. The silver salts of these acids are somewhat soluble in water, or can be made so by complexing with ammonia, amines, and the like. Silver nitrate, also used at times, is soluble in water as well. As the molecular weight of the acid increases, it generally becomes more organic in character and is no longer soluble to any appreciable extent in water. Such higher molecular weight acids can also form silver salts, but often they are not soluble in organic liquids. It has been found that organic acids having seven or more carbon atoms are useful in preparing silver catalysts. The tri-alkyl acetic acids, as discussed by Kirshenbaum in U.S. Pat. No. 2,955,949 are particularly effective, as will be seen in the examples. Such acids are available commercially as "neo-acids" and are formed from olefins by carbonylation and hydrolysis or by hydroformylation and oxidation. Since they are soluble in organic liquids their metal salts are used as paint driers and the like, where they are more stable than the naphthenic acid salts. The term "neo-acid" for purposes of this invention means that the carboxylic acid moiety is attached to a carbon atom, which is directly attached to three other carbon atoms, or to other carbon atoms, which are so attached. At least one of those carbon atoms will be part of a relatively long alkyl groups, which gives the compound its organic character. Neodecanoic acid is particularly preferred. As commercially available it is a mixture of 67% 2 ethyl 2 methyl heptanoic acid, 31% 2, 2 dimethyl octanoic acid, and 2% 2, 2 diethyl hexanoic acid. Other commercially available acids are neopentanoic acid and neoheptanoic acid. Generally, neo-acids having 7 carbon atoms or more are usable, although neo-decanoic acid is quite soluble and is preferred. The neo-acid configuration is considered necessary since those acids having only straight chains of carbon atoms appear to be so insoluble as to make preparation of high silver concentrations practically impossible.

As indicated, the silver is deposited upon the support by immersion of the support into a water-free hydrocarbon solvent containing a silver salt of a neo-acid until the solution has been absorbed into the pores of the support. Typical immersion times of from 1 to 60 minutes at temperatures of from 30° to 120° C. will usually suffice to achieve silver contents of as high as 7-15 wt %, as silver.

In addition to the silver salts, the liquid in which the support is immersed may contain promoters, such as alkaline earth metal promoters e.g. barium. Contrary to the usual silver solutions which contain water, it is characteristic of the present method to employ substantially water-free impregnating solutions, which will not readily dissolve the usual metal salts. However, it is feasible to prepare promoter metal salts of neo-acids which will be soluble in the solvent selected for use with the silver salts and thereby to introduce promoter metals into the silver impregnating solutions. Alternatively, the promoters may be added by post-deposition after the silver has been deposited, which permits some latitude in the solutions used, that is, once the silver has been deposited, it would be possible to use aqueous solutions to deposit water —soluble promoter metal salts.

Contrary to previous practice, it has been found that free acid should be avoided if the best catalyst performance is to be obtained. Previously, it was typical to include some free acid, e.g. lactic acid, along with the silver salt. In the present method, any free neo-acid, that is, unreacted with silver, will be separated, leaving substantially only the silver salt of the neo acid in the impregnating solution.

The catalysts are prepared by impregnating a support with a water-free hydrocarbon solution of a silver salt of the selected neo-acid, followed by activation of the impregnated silver. Subsequently, improved selectivity for oxidation of ethylene to ethylene oxide may be obtained by impregnating the activated silver catalyst with a solution of an alkali metal promoter, although this is not required.

In one embodiment, the selected neo-acid is reacted with silver oxide, or a basic silver salt e.g. silver carbonate. Although not essential, it has been found beneficial to include a solubilizing agent in the reaction mixture, such as alkanols, particularly ethanol or methanol. Conveniently, the reaction mixture will contain about 10 volume percent ethanol. Generally, it has been found that complete reaction of the silver with the acid is not achieved. While the formation of the silver salt at first proceeds rapidly, after about 20% of the acid has reacted the reaction is inhibited. To facilitate additional salt formation the silver salt which has been formed is separated from the reaction mixture by precipitation. This may be achieved by adding sufficient extra ethanol to the reaction mixture to precipitate substantially all of the silver salt which has been made. The precipitate may be removed by conventional means such as filtering or centrifuging and the solids washed free of residual acid.

Although the direct reaction of a silver compound with the neo acid as described above is preferred, the silver salt could be prepared by other methods familiar to those in the metal soap art such as the double decomposition or fusion methods.

The impregnating solution is prepared by redissolving the washed and dried precipitate in a hydrocarbon solvent, such as toluene, ethylbenzene, xylene, cyclohexane, or cumene. It is desirable that the solvent be capable of holding a large amount of the silver salt in order to permit preparation of silver catalysts having 7-15 wt % silver in a single impregnation. However, the proportions of solvent and the silver salt may be adjusted as may be convenient for preparation of the catalyst and are not considered critical. Typically a weight ratio of silver salt/solvent of 1/1-2/1 may be used, particularly about 2/1. Depending upon the solvent, the silver salt, and the ratio of the two, the temperature of the impregnating solution may be at room temperature or above to provide the desired results. A solvent should also be selected which can be conveniently removed and recovered for reuse.

Impregnation of the selected support is achieved in a conventional manner, that is, immersing the support in the silver salt solution described above for a period of time sufficient to saturate the pores of the support. The saturated support is removed from the solution and any excess drained off. After the silver salt has been applied to the support, the catalyst is activated by heating the impregnated particles to a sufficient temperature to remove the solvent and to decompose the silver salt, at least in part, to elemental silver.

Activation of the silver may be carried out by heating temperatures of about 200° to 600° C., preferably 250° to 500° C., in the presence of air or reduced oxygen atmospheres as desirable to control decomposition of the silver salts. The temperatures should be regulated so that the silver particles are highly active and suitable for oxidation of ethylene to ethylene oxide so that the catalyst can be used, even without the advantage obtained by post-deposition of an alkali metal(s). Preferably, the temperature will be raised gradually to a maximum of about 300° C., and held at the maximum temperature for a period of about one hour, until the silver particles have reached the desired size and all organic materials have been removed. In a particularly preferred procedure, the impregnated support is heated to about 100° C. over 1 hour, then to about 250° C. over two hours. Air will be passed over the silver-laden support during activation at a rate sufficient to assure oxygen is present at the surface of the support. Although air is the preferred gas, other gases may be used, but the presence of some oxygen is considered desirable. It is usual for the temperature to rise after decomposition of the silver salts has begun. This temperature excursion may be controlled by adjustment of the activation conditions. Activation of the impregnated support distributed as a thin-layer on a moving belt is particularly useful since by assuring uniform activation of the catalyst better average performance can be obtained.

When used the amount of alkali metal on the finished catalyst is generally similar to those employed heretofore. Thus, the amount deposited will be generally up to about $8 \times 10^{-3}$ gew/kg catalyst, preferably up to about $7 \times 10^{-3}$ gew/kg, and particularly about $1-6 \times 10^{-3}$ gew/kg (gew = gram equivalent weight). The alkali metals of the periodic table include sodium, lithium, potassium, rubidium, and cesium. For purposes of the present invention, the latter three alkali metals are particularly preferred, especially cesium, although sodium and lithium are not necessarily excluded. The alkali metal(s) will be supplied as metal compound(s) which maybe associated with various anions, as for example hydroxide nitrates, halides, formates, and acetates, particularly acetates. Conveniently, the alkali metal compounds are dissolved in water or alcohol-water solutions, and preferably ethanol water solutions containing only enough water to solubilize the alkali metal compound.

Catalysts prepared by the procedures described above have improved performance for use in the production of ethylene oxide by the vapor phase oxidation of ethylene with molecular oxygen. Oxidation reaction conditions such as those previously known in the art may be employed. These usually involve reaction temperatures of about 150°-400° C., usually 200°-300° C., and reaction pressures in the range of from 0.5-35 bar. Reactant feed mixtures usually contain 0.5-20% ethylene and 3-15% oxygen, with the balance comprising comparatively inert materials including such substances as nitrogen, carbon dioxide, methane, ethane, argon, and the like. Only a portion of the ethylene usually is reacted per pass over the catalyst and after separation of the desired ethylene oxide product and the removal of appropriate purge streams and carbon dioxide to prevent uncontrolled buildup of inerts and/or by-products, unreacted materials are returned to the oxidation reactor.

The following examples will illustrate the preparation and use of catalysts according to the invention and will support those aspects of the method previously disclosed as critical to achieving the desired results. Unless otherwise indicated, all parts and percentages are given by weight for liquids and solids, while for gases compositions are given as mol %, and flow rates are given in normal cubic meters per hour, i.e. at 0° and 760 mm Hg. The fraction of the ethylene converted to ethylene oxide is given as the percent selectivity, as is usual in the art.

EXAMPLE 1

A silver impregnating solution is prepared by dissolving 173 gm of silver oxide in a solution of 173 gm of absolute ethanol and 520 gm of neodecanoic acid obtained from Exxon Chemical Co., which contains 67% 2 ethyl 2 methyl heptanoic acid. 31% 2, 2 dimethyl octanoic acid, and 2% 2, 2 diethyl hexanoic acid. The neodecanoic acid and ethanol are mixed and heated to 80° C. The silver oxide is added in increments with vigorous stirring. Ten (10) drops of 30% hydrogen peroxide is added to clear the solution of prematurely reduced silver. Then 3000 gm of absolute ethanol is added to precipitate silver neodecanoate, which is filtered and then twice reslurried in 3000 gm of ethanol filtered and dried in air. About 85% of the silver oxide is recovered as silver neodecanoate. Two hundred seventeen (217) gm of silver neodecanoate powder are dissolved in 117 gm of toluene and the mixture is heated to 80° C. for impregnation of the support.

One hundred fifty (150) gm of the support material (Norton 5552 as ¼"×¼" rings) is preheated to 85° C. and immersed in the silver neodecanoate-toluene solution for 20 minutes. The saturated support is drained and subjected to a programmed heat treatment in air to decompose organic residue and deposit silver metal in a form suitable for the finished catalyst. The impregnated support is exposed for 1½ hours at 100° C. to evaporate toluene, then exposed to a temperature of 250° C. When a temperature of about 200–225° C. is reached, decomposition of the organic material begins, causing the temperature to rise to 335–350° C. After 30 minutes, the catalyst is removed from the source of heat and allowed to cool to room temperature.

In order to improve the performance of the freshly-activated silver catalyst it is impregnated with a solution of cesium acetate in a water-ethanol mixture. This solution is prepared by dissolving 4.19 gm of cesium acetate in 15.8 gm of distilled water. The resulting solution is mixed with 380 gm of anhydrous ethanol. The resulting solution has about 7000 ppm wt of cesium in solution. The described impregnating solution is circulated through a bed of the activated silver catalyst for 2 hours. The excess solution is drained and the catalyst is subsequently washed three times with pure anhydrous ethanol. The catalyst was dried and then ground to 12–18 mesh particles for testing. The catalyst contains 9% Ag, and 183 ppm Cs ($1.39 \times 10^{-3}$ gew/kg) by analysis. An additional 100 ppm (wt.) cesium was deposited by saturating the dry catalyst with a solution made from 0.005 gm of cesium acetate in 0.5 gm water and 9.8 gm ethanol.

A charge of 36 gm of this catalyst is placed in a reactor consisting of an u-shaped stainless steel tube 5.33 mm internal diameter heated in a molten salt bath. A feed mixture of 0.2% ethane, 14% ethylene, 6.7% oxygen, 5.5% carbon dioxide and 0.5 ppm ethylene dichloride and balance nitrogen was fed over the catalyst at a GHSV of 6000 hr$^{-1}$. The pressure was maintained at 20.4 bar and temperature was maintained between 230–280° C.

The results are shown in the following table.

TABLE 1

| Catalyst | Ag wt % | Cs wt. ppm | Reactor Temp. °C. | % EO Outlet | % Sel. |
|---|---|---|---|---|---|
| 1 | 9 | 260 | 236 | 1.52 | 82.3 |

EXAMPLE 2

If free neo-acid is present in the silver salt solution inferior catalysts have been produced, as will be seen from the following example.

A silver impregnating solution is prepared by reacting 80 gm of silver oxide with a solution of 240 gm of prime grade neodecanoic acid from Exxon Chemical Co. and 80 gm of absolute denatured ethanol from Ashland Chemical Co. The silver oxide was added over a period of 25 minutes. Thirty drops of 30% hydrogen peroxide was added to clear the solution. The solution was evaporated until a concentration of 23.2 wt % silver was reached. For each mol of silver neodecanoate formed, 3 mols of free neodecanoic acid remained. Instead of precipitating the silver neodecanoate as in Example 1, the solution was used directly to prepare a silver catalyst.

Three hundred (300) grams of Nortion 5552 catalyst support was immersed in the reduced solution just described. After withdrawing the impregnated support, the excess solution was drained off. Then, the support was heated in an oven in air at 130° C. for 2 hours, 200° C. for 2 hours, 260° C. for 2 hours, and 300° C. for 2 hours.

After cooling, the activated silver catalyst was post-impregnated with a cesium alcohol solution and tested as described in Example 1. The results are shown in the following table.

TABLE 2

| Catalyst | Ag. wt % | Cs ppm | Temp.°C. | % EO Outlet | % Sel. |
|---|---|---|---|---|---|
| 2 | 8.6 | 154 | 250 | 1.52 | 79.6 |

The results of the catalyst of Example 2 are inferior to that obtained in Example 1 where free neo-decanoic acid had been removed.

EXAMPLE 3

While the solvent would seem to be merely a vehicle for applying the silver neo-acid salt to the support, it has been found that the solvent also affects the performance of the finished catalyst, for reasons not understood at this time, but which may involve the decomposition of the silver salts. This example shows the effect of increasing molecular weight on alkyl derivatives of benzene used as solvents for silver neo-decanoate.

As in Example 1, silver neodecanoate is prepared as a solid and then 316 gms are dissolved in 166 gms of toluene. The resulting solution is used to impregnate 464 gms of Norton 5552 support. After draining excess solution, the impregnated support is activated by drying and heating to 250° C. in a forced air oven as in Example 1. The activated catalyst is post-impregnated with a water-ethanol solution of cesium acetate following the procedure of Example 1.

For comparison, a catalyst is prepared using xylene as a solvent. One hundred sixty five (165) gms of silver neodecanoate is dissolved in 110 gms of xylene and 194 gms of Norton 5552 support is impregnated as before. The impregnated support is activated by placing it as a single layer on a moving metal-mesh belt and exposing it to 500° C. air passing through the belt for about 2 minutes. After cooling, the activated catalyst is post-impregnated with a water ethanol solution of cesium acetate as before.

A third sample was made by dissolving 142 gms of silver neodecanoate in 95 gms of cumene and impregnating 220 gms of Norton 5552 support. The impregnated support is activated by exposing it to air at 500° C. for 2 minutes while lying on a moving belt. The activated catalyst was post-impregnated with a water-ethanol solution of cesium acetate as previously described.

Each of the finished catalysts were tested following the procedures of Example 1 with the following results:

TABLE 3

| Catalyst | Solvent | Ag. wt % | Cs, wt. ppm | Reactor Temp, °C. | % EO Outlet | % Sel. |
|---|---|---|---|---|---|---|
| 3 a | toluene | 10.3 | 356 | 248 | 1.56 | 81.5 |
| 3 b | xylene | 7.47 | 212 | 246 | 1.49 | 82.8 |
| 3 c | cumene | 8.2 | 259 | 236 | 1.51 | 83.5 |

Alkali and alkaline earth metals are well known as promoters for silver catalysts. Since prior art methods of catalyst preparation usually employed aqueous solutions it was possible to use commonly available alkali and alkaline earth metal compounds which are water soluble. Such compounds are not soluble in the organic solvents employed in preparing the catalyst of the invention. They may be used if they are converted to the alkali and alkaline earth metal salts of the neo-acid used to deposit silver, or some closely related analog, as will be seen from the following example.

EXAMPLE 4

The cesium salt of neodecanoic acid can be formed by adding 11.27 gm of an aqueous solution containing 50% cesium hydroxide to 6.50 gm of neodecanoic acid. A homogeneous solution results, which is evaporated to recover cesium neodecanoate crystals. These crystals are added to an organic solution containing silver neodecanoate and used to impregnate a support. Following the procedures of Example 1, 165 gm of silver neodecanoate is dissolved in 86.3 gm of toluene. The solution is filtered to remove undissolved solids and then 0.365 gm of cesium neodecanoate is added. A clear homogeneous solution results which is stable. The support is impregnated and then activated according to Example 1 to form a promoted silver catalyst which when analyzed is found to contain 250 ppm wt. cesium.

Although acid-base reactions to form silver salts of neo-acids are convenient, it is also possible to use other techniques, such as the double displacement method illustrated in the following example.

EXAMPLE 5

Sodium neodecanoate is formed by reacting 31.1 gm of neodecanoic acid with 7.2 gm of sodium hydroxide. The solution is diluted to 500 ml. with water. An aqueous solution of silver nitrate is prepared by dissolving 30.6 gm of silver nitrate in distilled water the diluting with water to a total volume of 500 ml. The two aqueous solutions are mixed, resulting in the formation of silver neodecanoate, which precipitates from the solution. The solids are filtered, washed with distilled water, and dried. Thereafter, they are used to prepare silver catalysts following the methods of the previous examples.

It has been found that practical difficulties limit the application of the process of the invention, which should not be considered merely an extension of prior art techniques to higher molecular weight carboxylic acids, as will be seen in the following examples.

EXAMPLE 6

The silver salt of neo-heptanoic acid is formed by reacting 3.87 gm of silver oxide with 50 gm of neo-heptanoic acid obtained from Exxon Chemical Co. in 15 gm of absolute ethanol in a hot water bath maintained at 80–85° C. After two hours some of the silver salt has precipitated, but to obtain dissolved salt 1000 ml. of additional ethanol is used to dilute the reaction mixture. Since the dissolved salt is insoluble in ethanol it precipates and is recovered by filtering and then washed with ethanol before use.

The silver neo-heptanoate is less soluble in hydrocarbon solvents than silver neo-decanoate. A saturated solution is prepared by dissolving 11 gm of silver heptanoate in 87 gm of toluene at 85° C. The solution is filtered to separate any undissolved solids and then used to prepare a silver catalyst. The maximum concentration of silver is only 1.5 wt %, making it difficult to obtain a catalyst having a typical silver content of 8–15 wt %.

EXAMPLE 7

The silver salt of neopentanoic acid is prepared following the procedure of Example 6. As before, the silver salt precipitated in the reaction mixture. The silver neopentanoate was found to be nearly insoluble in aromatic solvents, ethanol, acetone, and water. Consequently, silver catalysts could not be prepared according to the method of the invention.

The preparation was repeated using 2 ethyl hexanoic acid and decanoic acid and results similar to those obtained with silver neopentanoate are found.

The results obtained with the various acids above are summarized in the following table.

TABLE 4

| Acid | Structure | Maximum Solubility in Toluene gm salt/gm toluene |
|---|---|---|
| Neodecanoic | $R'-\underset{\underset{R'''}{\mid}}{\overset{\overset{R''}{\mid}}{C}}-COOH$ | 2:1 |
| Neoheptanoic | $R'-\underset{\underset{R'''}{\mid}}{\overset{\overset{R''}{\mid}}{C}}-COOH$ | 0.011:1 |
| Neopentanoic | $R'-\underset{\underset{R'''}{\mid}}{\overset{\overset{R''}{\mid}}{C}}-COOH$ | <0.001:1 |
| 2 Ethylhexanoic | $R'-\underset{\underset{H}{\mid}}{\overset{\overset{R''}{\mid}}{C}}-COOH$ | <0.001:1 |
| Decanoic | $R'-\underset{\underset{H}{\mid}}{\overset{\overset{H}{\mid}}{C}}-COOH$ | <0.001:1 |

From the above summary it can be seen that neodecanoic acid is particularly useful because the silver salt has substantial solubility in toluene, or similar aromatic solvents, making possible preparation of silver catalysts containing 8–15% silver. The other acids produce silver salts which are for practical purposes not useable. Consequently, it is considered that the silver salts of neo-acids will be useful only above about $C_7$ neo-acids. Silver neodecanoate is particularly preferred since the acid is readily availably commercially. However, other neo-acids which produce silver salts soluble in hydrocarbon solvents may be used and are considered within the scope of the invention.

EXAMPLE 8

Silver neodecanoate is especially useful since it is quite soluble in aromatic hydrocarbons and the neo-acid is commercially available. However, the silver salts of higher molecular weight neo-acids can be prepared and also appear to be soluble in aromatic hydrocarbons so that silver catalysts can be prepared.

The silver salt of neotridecanoic acid is formed by reacting 114.19 gms of silver oxide with 393 gms of neotridecanoic acid (obtained from the Exxon Chemical Co.) in 30 gms of absolute ethanol. As with neodecanoic acid, the neotridecanoic is not a pure compound and is believed to contain various acids having the "neo" configuration, as previously defined, and averaging about 13 carbon atoms. After refluxing for one hour, five drops of 30% hydrogen peroxide is added and a clear solution results. The mixture of silver neotridecanoate and unreacted neo-acid is mixed with an excess of ethanol (about 3000 cc) and the silver salt precipitates, making it possible to easily separate the silver salt from the unreacted acid. In contrast to silver neodecanoate which is distinctively crystalline and forms a suspension in ethanol, silver neotridecanoate forms a compressed tacky mass. The solid is washed with ethanol to remove most of the unreacted neo-acid.

A catalyst is prepared by dissolving 194.3 gms of silver neotridecanoate in 77.7 gms of cumene. The solution contains at least 20% more silver than is possible with silver neodecanoate. Two hundred seventy eight (278) gms of Norton 5552 support is impregnated with the silver solution in the usual manner. The impregnated support is activated on the previously described belt drier.

I claim:

1. A process for the oxidation of ethylene with molecular oxygen to ethylene oxide employing at oxidizing conditions a catalyst prepared by:
   (a) impregnating a support with a hydrocarbon solution of a silver salt of a neo-acid, having 7 or more carbon atoms, said solution being substantially free of water and said neo-acid, said support comprising alumina, silica, silica-alumina or combinations thereof;
   (b) separating the impregnated support of (a) from said solution and heating said separated support in the presence of molecular oxygen for a period of time sufficient to produce an active silver catalyst containing up to 15 wt. % silver.

2. The process of claim 1 wherein said silver salt is silver neodecanoate.

3. The process of claim 1 wherein said silver salt is dissolved in a hydrocarbon solvent selected from at least one member of the group consisting of toluene, xylene, ethylbenzene, cyclohexane, and cumene.

4. The process of claim 1 wherein said silver salt solution contains no more than about 0.1% water.

5. The process of claim 1 further comprising the steps of:
   (c) post-impregnating the activated catalyst of (b) with a solution of a compound of at least one alkali metal selected from the group consisting of Cs, K, and Rb and producing a finished catalyst containing up to about $8 \times 10^{-3}$ gew of said alkali metal for each kilogram of said finished catalyst.

6. The process of claim 5 wherein said alkali metal is cesium.

7. The process of claim 5 wherein said alkali metal content is about $1-6 \times 10^{-3}$ gew/kg of said finished catalyst.

8. The process of claim 1 further comprising the step of adding an alkali metal salt of a neo-acid to the impregnating solution of (a), said alkali metal being at least one selected form the group consisting of Cs, K, and Rb, in sufficient amount to produce a finished catalyst containing up to about $8 \times 10^{-3}$ gew of alkali metal for each kilogram of said finished catalyst.

9. The process of claim 8 wherein said alkali metal is cesium.

10. The process of claim 8 wherein said alkali metal content is about $1-6 \times 10^{-3}$ gew/kg of said finished catalyst.

* * * * *